(12) United States Patent
Brayton

(10) Patent No.: US 9,955,264 B2
(45) Date of Patent: Apr. 24, 2018

(54) HEADSET HEARING PROTECTION WITH INTEGRATED TRANSCEIVER AND SIREN ALERT DEVICE

(71) Applicant: Darryl Dwight Brayton, Richland, WA (US)

(72) Inventor: Darryl Dwight Brayton, Richland, WA (US)

( * ) Notice: Subject to any disclaimer, the term of this patent is extended or adjusted under 35 U.S.C. 154(b) by 139 days.

(21) Appl. No.: 14/251,454

(22) Filed: Apr. 11, 2014

(65) Prior Publication Data

US 2015/0055784 A1 Feb. 26, 2015

Related U.S. Application Data

(60) Provisional application No. 61/810,712, filed on Apr. 11, 2013.

(51) Int. Cl.

| H04R 5/00 | (2006.01) |
|---|---|
| H04R 5/033 | (2006.01) |
| H04R 29/00 | (2006.01) |
| H04R 1/10 | (2006.01) |
| G10L 13/00 | (2006.01) |

(52) U.S. Cl.
CPC .............. *H04R 5/033* (2013.01); *G10L 13/00* (2013.01); *H04R 1/1083* (2013.01);
(Continued)

(58) Field of Classification Search
None
See application file for complete search history.

(56) References Cited

U.S. PATENT DOCUMENTS 5,970,155 A * 10/1999 Leppalahti ...................... 381/72
2005/0238181 A1* 10/2005 Nilsson et al. ................ 381/72
(Continued)

*Primary Examiner* — Muhammad N Edun
(74) *Attorney, Agent, or Firm* — Eugenio J. Torres-Oyola; Victor Rodriguez-Reyes; Ferraiuoli LLC

(57) ABSTRACT

Systems and methods of alert and notification transmission are contemplated in which a transceiver provides an alert/notification to a user(s) wearing a headset that provides hearing protection device with an integrated transceiver (e.g., radio) and on-board siren-voice alert function board. Typically, this device would be used in a loud noise area (>+70 dB) that would otherwise prevent the user from hearing an alert and notification, such as a siren tone and/or Public Address announcement. While the alert and notification is silent, the device is contemplated to provide sufficient hearing protection (>+15 dB) from the ambient surroundings. It is also contemplated that it could play local music through an audio input port/other receiving method. When an alert and notification command is communicated to a headset device's address (or globally) through the transceiver, the device(s) would then proceed to play, within the headset, the desired alert and notification message. This would be successful, as the ambient sound is suppressed around the wearer and the message clearly listened too, live and/or pre-recorded. The alert could also be in the form of a visual indication (e.g. LEDs, etc.), vibration, etc. generated from this same function board. The transceiver could be an unlicensed frequency (e.g., Wi-Fi, FRS, etc.) or a licensed frequency (VHF, UHF, Digital 800 MHz, etc.), and while preferred to be bi-directional communications, it could also function in an alert only mode. Further, by adding a GPS locator, a facility and/or site could give proximity warnings based on user skill level in negotiation the facility, perhaps based on training level and experience. Also, digital messages are contemplated where text messages could be converted to speech.

22 Claims, 4 Drawing Sheets

(52) U.S. Cl.
CPC ...... *H04R 29/008* (2013.01); *H04R 2201/107* (2013.01); *H04R 2420/07* (2013.01); *H04R 2430/01* (2013.01)

(56) References Cited

U.S. PATENT DOCUMENTS

| | | | |
|---|---|---|---|
| 2006/0212998 A1* | 9/2006 | Gath | 2/423 |
| 2011/0209273 A1* | 9/2011 | Fountain | A61F 11/14 2/423 |

* cited by examiner

HEADSET HEARING PROTECTION WITH INTEGRATED TRANSCEIVER AND SIREN ALERT DEVICE

STATEMENT REGARDING FEDERALLY SPONSORED RESEARCH AND DEVELOPMENT

N/A

RELATED APPLICATIONS

N/A

FIELD OF THE INVENTION

The field of the invention is devices and methods for hearing protection and personnel alert and notification.

BACKGROUND OF THE INVENTION

All or almost all of the currently known alert systems are limited, especially in high noise areas of plant and facilities, in trying to mitigate the noise levels produced by the equipment and/or processing in an immediate vicinity where workers are located.

Further exacerbating this issue, is the fact the workers are issued hearing protection to protect against hearing loss. Typically, these are in the form-factor of "earmuffs" made of hardened plastic ear cups, with foam filling, that provide about +25 dB sound reduction to the worker. These earmuffs can be worn outside of, inside of, or on (via clips on the left and right side), their construction hard-hats. As a result of this, many large companies, in processing industries, spend money on a) additional sound producing speakers and/or sirens to overcome the ambient noise, or b) add visual indicators to alert workers.

Neither approach does a sufficient job in providing alert and notification to protect workers. The additional sound is typically not enough to differentiate from the ambient noise, and is less effective if the worker wears sound hearing protection equipment. The visual alerts are only effective if in the visual field of the workers.

The workplace has also experimented with integrated radios in the headset. This can perform the required alert and notification within the hearing range of the user. However, it is not an integrated device in the alert and notification system per se, and would require separate systems integration and separate radio channels dedicated to that purpose, especially for targeted and addressed broadcasts to specific areas where an emergency exists and/or a proximity limit was exceeded.

Therefore, while numerous devices and methods for alert and notification in high noise areas are known in the art, all or almost all of them, suffer from one or more disadvantages. Therefore, there is still a need for improved devices and methods to provide alert and notification to personnel in high noise environments.

SUMMARY OF THE INVENTION

Systems and methods of alert and notification transmission are contemplated in which a transceiver provides an alert/notification to a user(s) wearing a headset that provides hearing protection device with an integrated radio transceiver and on-board siren-voice alert function board. Typically, this device would be used in a loud noise area (>+70 dB) that would otherwise prevent the user from hearing an alert and notification, such as a siren tone and/or Public Address announcement.

While the alert and notification is silent, the device is contemplated to provide sufficient hearing protection (>+70 dB) the ambient surroundings. It is also contemplated that it could play local music through an audio input port/other receiving method.

When an alert and notification command is communicated to a headset device's address (or globally) through the transceiver, the device(s) would then proceed to play, within the headset, the desired alert and notification message. This would be successful, as the ambient sound is suppressed around the wearer and the message clearly listened too, live and/or pre-recorded.

The alert could also be in the form of a visual indication (e.g. LEDs, etc.), vibration, etc. generated from this same function board.

The transceiver could be an unlicensed frequency (e.g., Wi-Fi, FRS, etc.) or a licensed frequency (VHF, UHF, Digital 800 MHz, etc.), and while preferred to be bidirectional communications, it could also function in an alert only mode.

Further, by adding a GPS locator, a facility and/or site could give proximity warnings based on user skill level in negotiation the facility, perhaps based on training level and experience.

Also, digital messages are contemplated where text messages could be stored for secondary command playback at a later time, or immediately converted from text to speech for playback. The text storage could then be connected to heads-up safety glasses that allow text input from the output of the device to display the message in text format.

Among other suitable uses for said device would be envisioned to be factories, refineries, on-board ships and other marine vehicles, flight lines, runaways and aircraft carriers with jet, propeller, turbo-prop and helicopter aircraft, and outdoor events with high noise levels, e.g., concerts, etc.

Among other suitable uses for said device would be to issue to visitors and subcontractors at a processing facility and/or factory that would reduce training times for emergency response, and give specialized warnings based on proximity and the user training and experience level. For example, if a visitor wandered into a contaminated area the on-board GPS would broadcast position to a central command station that would then broadcast to that device's address to back away from the area, or wait for help to arrive, etc.

DETAILED DESCRIPTION

A device worn on the ears to provide hearing protection and alerting and notification, including proximity alerts, to the wearer in various formats such as audible, voice, visual, vibration, text to speech, etc.

The inventor has discovered that hearing protection can be configured to provide alert and notification functions at the field, especially in high ambient noise areas that are cost prohibitive to alert by other existing means. The systems and methods of alert and notification transmission, in accordance with the principles of the present disclosure, are intended to include a transceiver which provides an alert/notification to a user(s) wearing a headset that provides hearing protection device, wherein said hearing protection device comprises an integrated radio transceiver and on-board siren-voice alert function board. Typically, this hearing protection device would be used in a loud noise area, for example areas were the decibel are above 70 dB (>+70 dB), wherein said loud sound prevent the user from hearing an alert and notification, such as a siren tone and/or Public Address announcement. In accordance with the principles of the present invention the hearing protection device, worn over and/or in the ears, provides sound reduction from ambient noise levels of 15 decibels (>+15 dB), that also functions as an alert and notification device in all circumstances, but especially for loud noise areas (>+70 dB). It is also contemplated that said device could play local talk/music through an audio input port/other receiving method while waiting for an alert and notification to its device address.

Figure 1A:
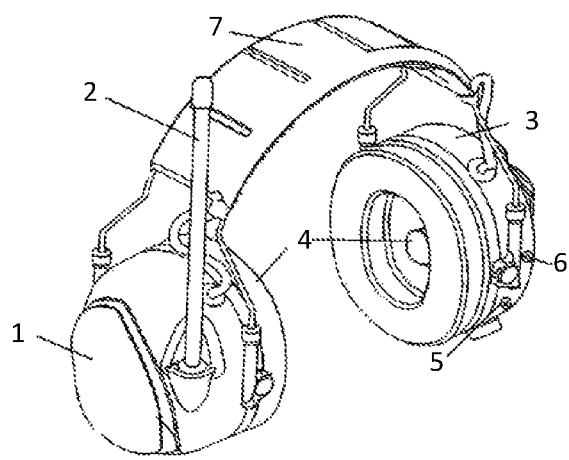
FIG. 1A is a schematic of an exemplary hearing protector and alert and notification device.

Refer to FIG. 1A. Most preferably, the integrated transceiver 1 and antenna 2 can be any transceivers that may be configured to fit in the space provided by the plastic cup forming the earmuff shell E. Therefore, most typically, preferred low-range transceivers will operate using the family radio spectrum of frequencies (462 and 467 MHz) (alternatively Bluetooth and other low-power mesh networks) having a maximum effective radiated power of 0.5 W. In such cases, the low-range transceiver will typically have a service area (low-range notification zone) of less than 20 km and more typically less than 10 km as measured as linear distance between the low-range transmitter and a receiver/transceiver that receives the signal from the low-range transceiver. However, in other preferred aspects of the inventive subject matter, the low-range transceiver may also operate at numerous alternative frequencies and bands, including microwave bands (e.g., 800 MHz band), VHF and UHF frequencies at a power output of 0.1-100 W, and even more, based on technology advances. With respect to the term "transceiver" as used herein, it should be noted that this term generally refers to a device that is configured to receive and transmit radio signals. However, in other preferred aspects, devices that are configured to only receive radio signals are also included in the definition of the term "transceiver".

Figure 2:
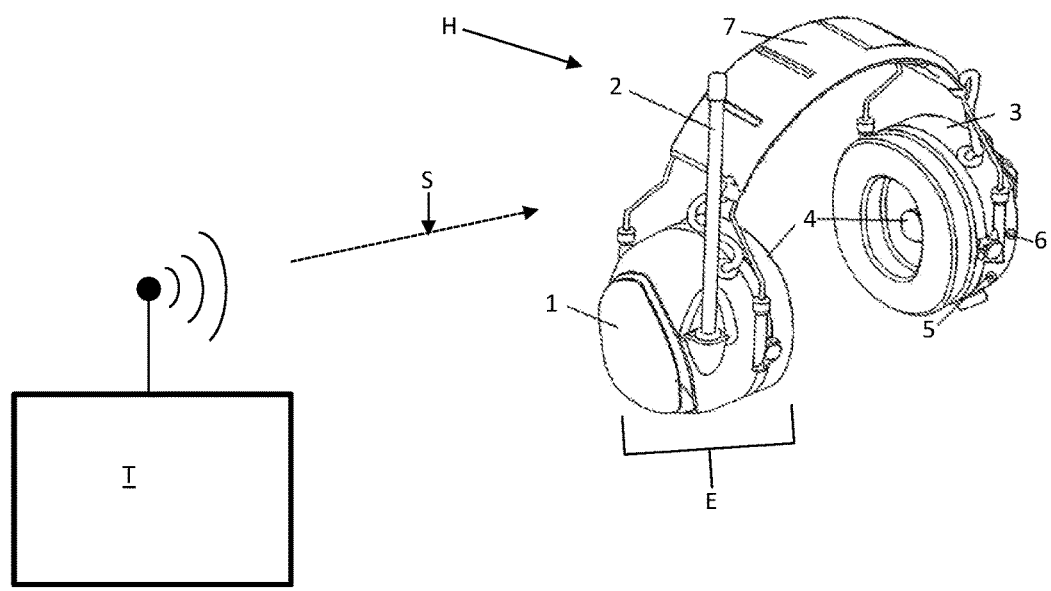
FIG. 2 is an exemplary embodiment of the hearing protector and alert and notification device receiving a signal from the transmitter in accordance with the principles of the present disclosure.
Figure 3:
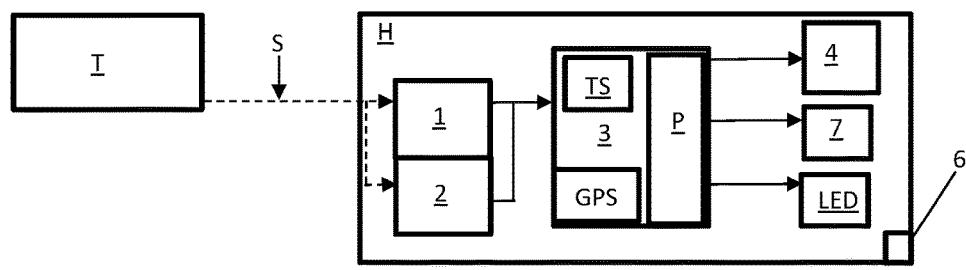
FIG. 3 is a block diagram of an exemplary hearing protector and alert and notification device receiving a signal from the transmitter in accordance with the principles of the present disclosure.

The integrated radio transceiver 1 and on-board siren-voice alert function board 3 receives and processes the addressed alert and notification. As shown on FIG. 2, when an alert and notification command S is communicated to a headset device's address (or globally) through the transceiver 1, the headset device(s) would then proceed to play, within the headset, more particularly through the headphones 4 the desired alert and notification message. This would be successful, as the ambient sound is suppressed around the wearer and the message clearly listened too, live and/or pre-recorded. For example, an alert is sent from the operations group warning of an emergency situation. The device receives the signal S, as shown in FIG. 3 on the antenna 2 and the integrated transceiver 1 and passes to the function board 3. The function board 3 checks for the address and then performs the appropriate alert and notification function as configured by its on-board computer processor P in the function board 3. Also, the function board 3 comprises a GPS locator which facility and/or site-specific proximity warnings based on user skill level in negotiation of the facility, based on training level and experience. Further, the function board 3 comprises a text-to-speech converter TS which could store text messages for later playback by secondary command string for text to speech playback. The text-to-speech converter TS also would immediately play text messages converted to speech, and allow for connection to heads-up safety glasses that allow text input from the output 6 of the device H to display the message in text format.

Therefore, the system comprises a hearing protection and alert and notification device H and a transceiver T, wherein said transceiver T broadcast and alert and notification message to the preprogrammed address of said device H to provide at least one of the following; (a) visual indication alert and notification comprising an light emitting diode LED, (b) tone audio alert and notification, (c) live or pre-recorded voice alert and notification, (d) text to speech alert and notification, and/or (e) vibration alert and notification comprising a vibrating strip 7.

The sound is played in either mono or stereo mode through the headphones 4 integral to the plastic cups, with insulation filling the cups providing the requisite protection against high ambient noise.

An optional input is provided for a secondary audio source 5, and an optional port 6 for text output through an ASCII protocol (such as RS-232, others) provides for a text driver for anticipated heads-up safety glasses. Other functions, such as vibration strips 7 can be placed in the headband area, for example.

Figure 1B:
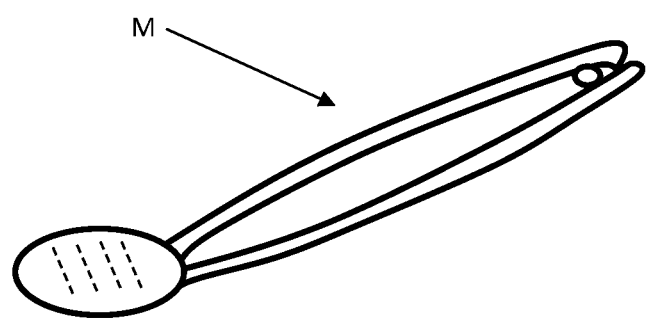
FIG. 1B is a schematic of an exemplary hearing protector and alert and notification device boom microphone that optionally attaches to FIG. 1A.

Refer to FIG. 1B. An optional boom microphone could be attached to the headset of FIG. 1A to provide bi-directional communication to allow a wearer of said device to further communicate with base operations during an emergency alert and notification. Further the microphone may be integrated to give the ability to communicate to a base for further instructions.

Figure 4:
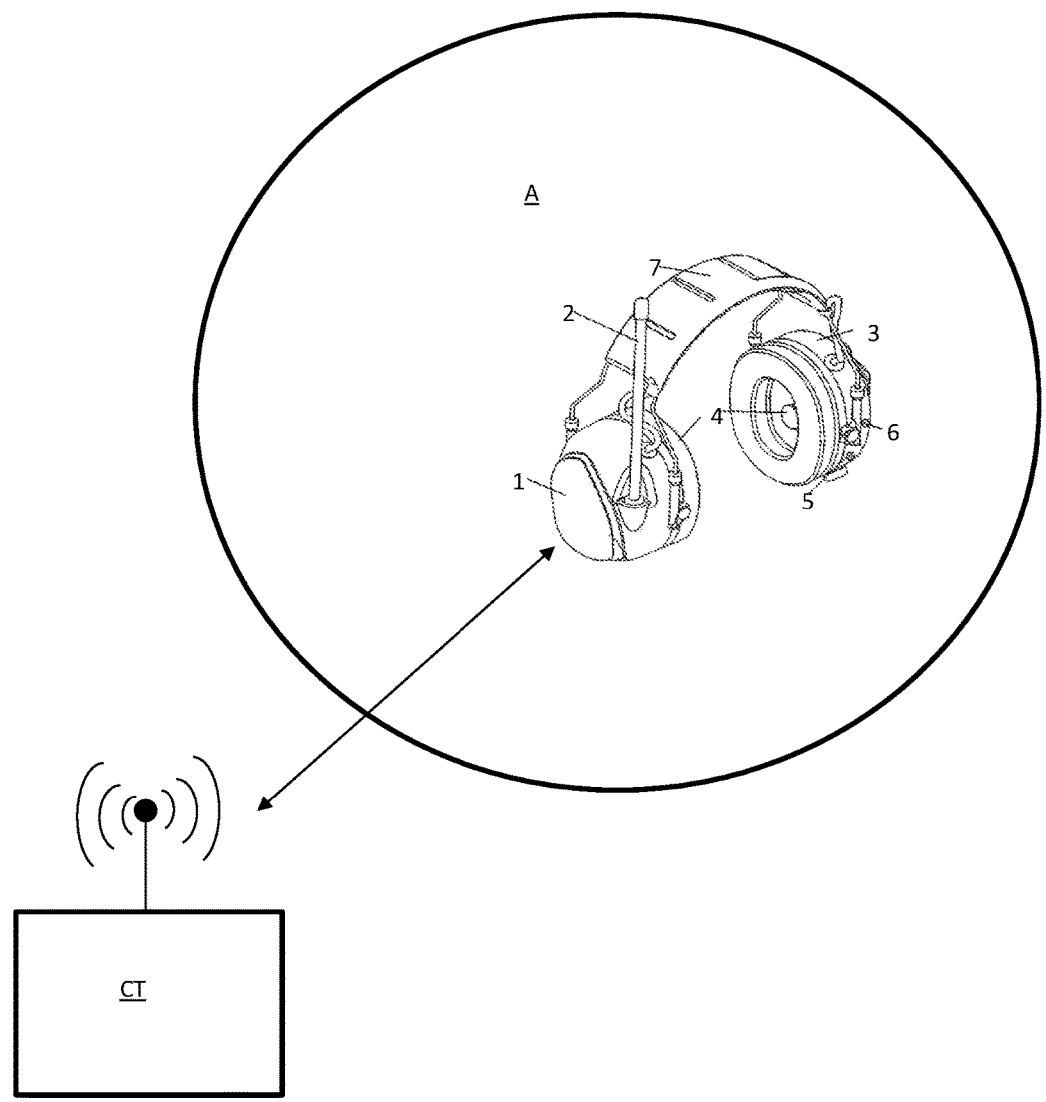
FIG. 4 is a schematic of an exemplary hearing protector and alert and notification device receiving broadcasting position to a central command station, wherein said central command station further broadcast back to de device to back away from a contaminated area in accordance with the principles of the present disclosure.

As explained above among other suitable uses for said device H would be to issue to visitors and subcontractors at a processing facility and/or factory that would reduce training times for emergency response. As shown in FIG. 4, the present device is configured to warned based on proximity and the user training and experience level. For example, if a visitor wandered into a contaminated area A the on-board GPS would broadcast position to a central command station CT that would then broadcast to that device's address to back away from the area A, or wait for help to arrive, etc.

Figure 5:
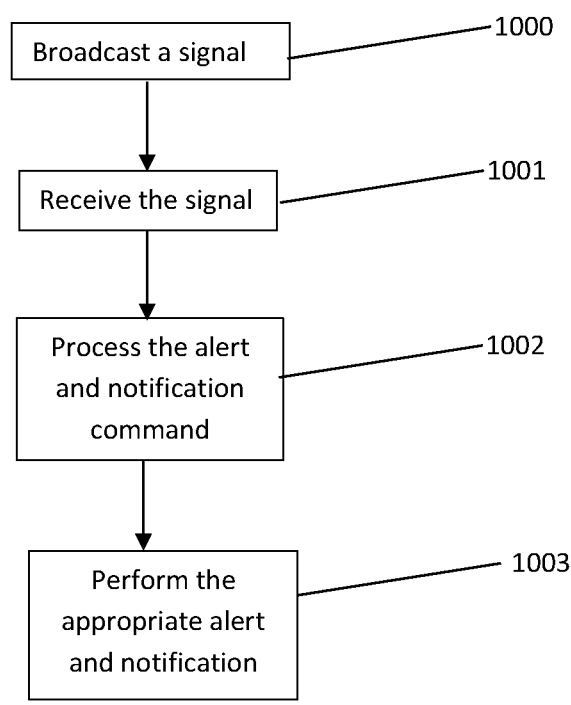
FIG. 5 is a flow chart of an exemplary hearing protector and alert and notification device receiving a signal from the transmitter in accordance with the principles of the present disclosure.

FIG. 5 is directed to flow chart of an exemplary hearing protector and alert and notification device receiving a signal from the transmitter in accordance with the principles of the present disclosure. As mentioned above a transmitter 1 broadcast a signal 1000 including an alert and notification command S communicated to the headset device H. The headset device H receives the signal 1001. The headset device H process the signal 1002. In accordance with the principles of the present invention, as mentioned above, the headset device H by means of a function board 3 checks for the address and then performs the appropriate alert and notification function 1003 as configured by its on-board computer processor P in the function board 3.

Also, it should be apparent that the alert and notification device H, could be packaged local to the user (e.g., removed from the ear cup and worn on a different part of the user's body, say a belt) but still be integrated and connected either by wire or wireless to the headset and performing the same overall integrated function. Thus, specific embodiments and applications of hearing protection with integrated transceivers and alert and notification function board for addressable play-back device(s) have been disclosed. It should be apparent, however, to those skilled in the art that many more modifications besides those already described are possible without departing from the inventive concepts herein. The inventive subject matter, therefore, is not to be restricted except in the spirit of the appended claims.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

The invention claimed is:

1. A hearing protection and alert and notification device comprising:
    a headset device, wherein said headset device comprises:
        an antenna;
        an ambient sound suppressor, wherein said ambient sound suppressor comprises headphones;
        wherein said ambient sound suppressor comprises a local to a user and integrated radio transceiver for receiving a particular signal including an address;
        wherein said ambient sound suppressor comprises a local to the user and integrated function board; wherein said integrated function board comprises a processor, wherein said processor comprises a preprogrammed address; and
        wherein said integrated function board is configured to verify said particular signal and generate an alert signal.

2. The hearing protection and alert and notification device as in claim 1, wherein said particular signal comprises an address; wherein said address is related to said preprogrammed address.

3. The hearing protection and alert and notification device as in claim 1, wherein said alert is selected from group consisting of a visual indication alert and notification, a tone audio alert and notification, a voice alert and notification, a text to speech alert and notification or a vibration alert and notification comprising a vibrating strip 7.

4. The hearing protection and alert and notification device as in claim 3, wherein the visual indication alert and notification comprises a light emitting diode.

5. The hearing protection and alert and notification device as in claim 3, wherein said voice alert is selected from group consisting of a live voice alert and notification or a pre-recorded voice alert and notification.

6. The hearing protection and alert and notification device as in claim 3, wherein said vibration alert and notification comprises a vibrating strip.

7. The hearing protection and alert and notification device as in claim 1, wherein said ambient sound suppressor comprises earmuffs.

8. The hearing protection and alert and notification device as in claim 7, wherein said earmuffs are configured to protect the user from loud noises.

9. The hearing protection and alert and notification device as in claim 8, wherein said loud noises are above 70 decibels.

10. The hearing protection and alert and notification device as in claim 1, comprises an audio input.

11. The hearing protection and alert and notification device as in claim 1, wherein said function board comprises a global position system locator.

12. A system for alert transmission comprising:
    a first transceiver generating a notification to an user;
    a hearing protection device, wherein said hearing protection device comprises:
        a headset device, wherein said headset device comprises:
            an antenna for receiving said notification including an address;
            an ambient sound suppressor, wherein said ambient sound suppressor comprises headphones;
            wherein said ambient sound suppressor comprises a local to the user and integrated radio transceiver coupled to said antenna for receiving said notification;
            wherein said ambient sound suppressor comprises a local to the user and integrated function board, wherein said integrated function board comprises a processor, wherein said processor comprises a preprogrammed address; and wherein said integrated function board is configured to verify said address and generate an alert signal at said hearing protection device.

13. The system for alert transmission as in claim 12, wherein said address is related to said preprogrammed address.

14. The system for alert transmission as in claim 12, wherein said alert is selected from group consisting of a visual indication alert and notification, a tone audio alert and notification, a voice alert and notification, a text to speech alert and notification or a vibration alert and notification comprising a vibrating strip 7.

15. The system for alert transmission as in claim 14, wherein the visual indication alert and notification comprises a light emitting diode.

16. The system for alert transmission as in claim 14, wherein said voice alert is selected from group consisting of a live voice alert and notification or a pre-recorded voice alert and notification.

17. The system for alert transmission as in claim 14, wherein said vibration alert and notification comprises a vibrating strip.

18. The system for alert transmission as in claim 12, wherein said ambient sound suppressor comprises earmuffs.

19. The system for alert transmission as in claim 18, wherein said earmuffs are configured to protect an user from loud noises.

20. The system for alert transmission as in claim 19, wherein said loud noises are above 70 decibels.

21. The system for alert transmission as in claim 12, comprises an audio input.

22. The system for alert transmission as in claim 12, wherein said function board comprises a global position system locator.

\* \* \* \* \*